US006563122B1

(12) United States Patent
Lüdeker et al.

(10) Patent No.: US 6,563,122 B1
(45) Date of Patent: May 13, 2003

(54) FLUORESCENCE DETECTION ASSEMBLY FOR DETERMINATION OF SIGNIFICANT VEGETATION PARAMETERS

(75) Inventors: Wilhelm Lüdeker, Windach (DE); Kurt Günther, Gilching (DE); Hans-Günter Dahn, Grünwald (DE)

(73) Assignee: Deutsches Zentrum fur Luft-und Raumfahrt E.V., Köln (DE)

( * ) Notice: Subject to any disclaimer, the term of this patent is extended or adjusted under 35 U.S.C. 154(b) by 0 days.

(21) Appl. No.: 09/830,697

(22) PCT Filed: Oct. 28, 1998

(86) PCT No.: PCT/EP98/06815

§ 371 (c)(1),
(2), (4) Date: Apr. 30, 2001

(87) PCT Pub. No.: WO00/25114

PCT Pub. Date: May 4, 2000

(51) Int. Cl.[7] ............................................ G01N 21/64
(52) U.S. Cl. .................................. 250/458.1; 250/459.1
(58) Field of Search .......................... 250/458.1, 459.1, 250/461.1

(56) References Cited

U.S. PATENT DOCUMENTS

| | | | |
|---|---|---|---|
| 4,650,336 A | 3/1987 | Moll | |
| 4,769,700 A | 9/1988 | Pryor | |
| 5,096,293 A | 3/1992 | Cecchi et al. | |
| 5,412,219 A | 5/1995 | Chappelle | |
| 5,636,792 A | 6/1997 | Sauter | |
| 5,682,038 A | * 10/1997 | Hoffman | 250/458.1 |

FOREIGN PATENT DOCUMENTS

EP    0 215 399    3/1987

OTHER PUBLICATIONS

Mazzinghi, "A laser diode fluorometer for field measurements of the F685/F730 chlorophyll fluorescence ratio", *Review of Scientific Instruments*, (1996), vol. 67, No. 10, pp. 3737–3744.

Edner et al., "Fluorescene lidar multicolor imaging of vegetation", *Applied Optics*, (1994), vol. 33, No. 13, pp. 2471–2479.

Ning et al., "Imaging fluorometer to detect pathological and physiological changes in plants", *Applied Spectroscopy*, (1995), vol. 49, No. 10, pp. 1381–1389.

1996 International Geoscience and Remote Sensing Symposium (Igarss '96), Lincoln, NE, US May 27–31, 1996, vol. 3, pp. 1812–1815.

* cited by examiner

*Primary Examiner*—Constantine Hannaher
*Assistant Examiner*—Timothy Moran
(74) *Attorney, Agent, or Firm*—Browdy and Neimark

(57) ABSTRACT

A basic assembly configuration for determination of relevant vegetation parameters includes a high repetitive pulsed excitation laser (1) for the stimulation of chlorophyll fluorescence, a fluorescence detector (3) including an imaging and separation optic (4, 5), a trigger and delay electronic (6) to adjust the laser and appropriate detector timing and a detector electronic (7), consisting of a signal recording and processing module. The assembly can be used for determination of relevant vegetation parameters for agricultural, horticultural and greenhouse application.

57 Claims, 4 Drawing Sheets

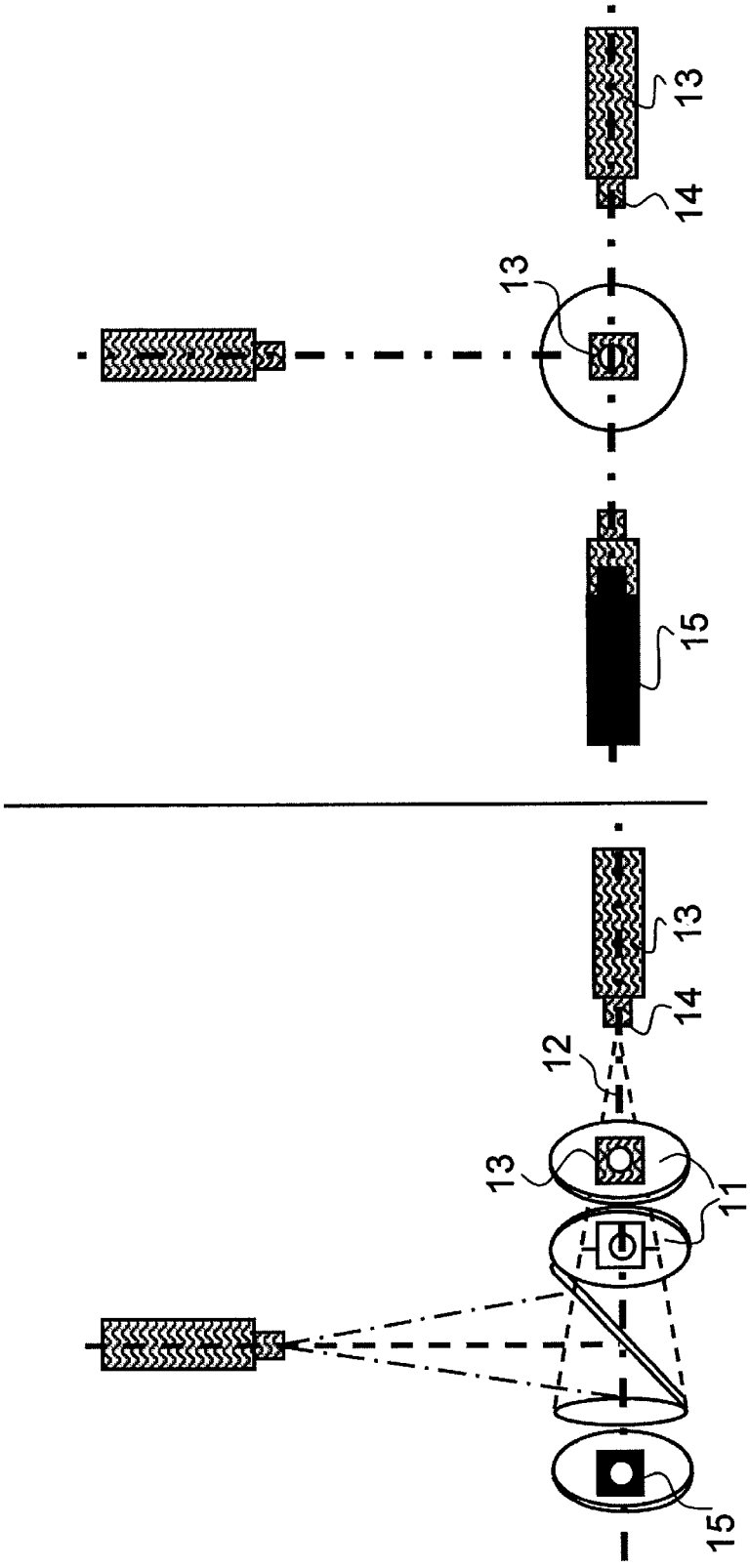

FLUORESCENCE DETECTION ASSEMBLY FOR DETERMINATION OF SIGNIFICANT VEGETATION PARAMETERS

REFERENCE TO RELATED APPLICATIONS

The present application is the national stage under 35 U.S.C. 371 of international application PCT/EP98/06815 filed Oct. 28, 1998 which designated the United States, and which international application was published under PCT Article 21(2) in the English language.

BACKGROUND OF THE INVENTION

This invention relates to a fluorescence detection assembly for determination of relevant vegetation parameters comprising an excitation source consisting in a low power laser device with an excitation wavelength in the red spectral region, a beam forming optical device, a dichroic beam splitter, a basic fluorescence detector system including an entrance optical device receiving fluorescence emission via said dichroic beam splitter and an interference filter blocking out the elastic back scatter signal, an electronic detection device for detecting a fluorescence signal, and an electronic trigger and timing device.

First of all the phenomenon of chlorophyll fluorescence will be discussed now.

The absorbed photosynthetic active radiation (PAR) of the solar irradiation (380 nm<$\lambda$<750 nm) is used by plants primarily to convert the absorbed energy in chemically bound energy (photosynthesis) and stored as chemical energy. This process is directly linked with the uptake of carbon dioxide and the release of oxygen (called primary productivity). Two other pathways are possible for the absorbed energy to keep plants energetically balanced. First, the emission of thermal energy and second, the emission as fluorescence light may be used for regulation.

The thermal energy budget is filled up with solar energy from the visible (VIS) and the short wave infrared (SWIR) range of the solar spectrum. SWIR radiation is directly absorbed by the leaf internal water content. The VIS range contributes via the exciton transfer inside the antenna pigment of the reaction centers (PS I; PS II) and light harvesting complex (LHPC). In this process the absorbed photon energy is transformed to energy quantities required by PS I and PS II. The surplus of energy is stored in oscillating and rotation energy levels and thus finally converted into heat.

At the PS I and PS II the absorbed energy quantities may be used by the so called light reactions, may be transferred to heat or finally emitted as fluorescence light. The emitted fluorescence in the red spectral region is due to the chlorophyll molecules associated to PS I, PS II and the LHPC. The conversion probabilities for heat and fluorescence are considered constant in time, whereas the conversion rate at the light reaction is considered as a function of the state of the reaction center (electron transfer chain) and the phosphorylation state of the photosynthetic active cell membranes. The following Equation (1) will describe the fraction of sun induced chlorophyll fluorescence light ($F_{Sun}(t)$) which is emitted by the reaction centers:

$$F_{Sun}(t) = \frac{k_{Fluorescence}}{k_{Fluorescence} + k_{Heat} + k_{Photosynthesis}(\Phi, M)} * \int_{PAR} I_{Abs-Sun} d\lambda \quad (1)$$

$k_i$: conversion probability for fluorescence, heat and photosynthesis $\phi(t)$: state of the reaction center $M(t)$: phosphorylation of membrane $I_{Abs-Sun}$: absorbed spectral irradiance.

From this formula it can be seen that the behaviour of the time dependent chlorophyll fluorescence gives access to the relative changes of the photosynthetic activity if one assumes that "$\phi$" and "M" are functions of time.

Detection and interpretation of the chlorophyll fluorescence intensity will be discussed now.

The detection of sun-induced chlorophyll fluorescence is difficult due to the fact that the fluorescence signal is superimposed by the reflected light (passive spectrum). For leaves or plant canopies the fluorescence signal is of the order of only some percent compared to the total signal. Therefore, different measuring techniques applying additional light sources were developed in the past for using the chlorophyll fluorescence for different applications.

In general, a modulated or pulsed light source is added to the sun irradiation "$I_{Abs-Sun}$" inducing a modulated or pulsed fluorescence signal $F_{add}(t)$ which superimposes the sun induced fluorescence $F_{Sun}(t)$ and the reflected signal IR($\lambda$). Applying a laser source for excitation the so called laser induced fluorescence (LIF) is generated. Equation (1) is then modified to:

$$F_{Sun}(t) + F_{add}(t) = \frac{k_{Fluorescence}}{k_{Fluorescence} + k_{Photosynthesis}(\Phi, M)} * \int_{PAR} (I_{Abs-Sun} + I_{add}) d\lambda.$$

The total signal which is normally detected is given by the sum of all fluorescence signals and the reflected signal IR($\lambda$). With adequate technical set-up the fluorescence signal excited by an additional light source can be separated from the passive spectrum and the sun induced fluorescence even under daylight conditions at distances, ranging from direct contact (Schreiber 1986, Patent DE 3518527, Mazzinghi 1991, EP 0 434 644 B1) to one meter (Chappelle 1995, U.S. Pat. No. 5,412,219) and several hundred meters (Cecchi and Pantani 1995, EP 0 419 425 B1).

The technical challenge for all systems either for contact measurements as well as for remote measurements is to install an excitation set-up strong enough to induce a sufficiently intense fluorescence signal in order to overcome the passive spectrum and weak enough to keep the photosynthetic system in an unchanged physiological status.

DESCRIPTION OF STATE OF THE ART

In the well known pulse-amplitude-modulation (PAM) fluorometer (Schreiber et al. 1986, Patent DE 3518527) a weak measuring light (light emitting red diode LED) induces the chlorophyll fluorescence via an optical fiber without changing the photosynthetic state of the plant. The fluorescence is transmitted by an optical fiber to a photodiode which detects all fluorescence light above 700 nm. For dark adapted plants no photosynthetic activity is stimulated when the measuring light is on.

Illumination of a dark adapted leaf with an intense flash of several milliseconds up to some seconds duration (called saturating light pulse) gives the maximum available fluorescence (called: Fm) but does not induce photosynthesis. A continuous illumination with non saturating light (called: actinic light) induces photosynthetic activity. After several seconds until minutes of illumination all contributing processes are in equilibrium with the supplied light and thus the fluorescence has reached a steady state value Fs. The transient of the fluorescence during illumination of dark adapted leaves is called Kautzky effect. For example FIG. 1 shows a measured diagram of a Kautzky kinetic of a cucumber plant. The detected fluorescence at 685 nm is exclusively induced by the laser pulses. Illumination with a 500 W halogen spot light influence the photosynthetic state only and thus $k_{Photo}$. Its contribution to the fluorescence signal, especially as excitation source, is negligible. The PAM fluorometer is normally operated in direct contact with leaves but can be used also at distances of some centimeters.

Detection and interpretation of the Red Fluorescence Ratio will be discussed now.

When excited by UV light, the typical fluorescence spectrum of a plant exhibits two dominant emission bands (FIG. 2), one from 400 nm–600 nm (called: blue-green fluorescence BG) and one from 650 nm–800 nm (called: red fluorescence; F685, F730). For example FIG. 2 shows a diagram of the fluorescence emission spectrum of a maize plant grown in the greenhouse. The fluorescence at 685 nm and at 730 nm (called: F685 and F730) originates exclusively from the leaf internal-chlorophyll. The blue-green fluorescence (BG) is emitted primarily by phenolic components of the cell walls.

The emission features of healthy plants are closely coupled to the plant morphology, as e.g. the pigment constituents and pigment concentration. Additional features may occur when plants are infected by fungi.

From experiments it is known, that the emissions at 685 and 730 nm are both linked to the photosynthetic system as described before and thus show nearly the same variation in time. In contrast the fluorescence ratio F685/F730 of an individual plant or leaf is constant in time and depends only on the optical properties of the leaf (Equation (2)).

$$\frac{F685}{F730} = \psi_{730}^{685} A \frac{e^{-(\beta 1 + c*\alpha 1)d} - 1}{e^{-(\beta 2 + c*\alpha 2)d} - 1} \quad (2)$$

with:

ψ:=spectral fluorescence characteristic @λ=685 and 730 nm

β:=scattering coefficient @λ=685 and 730 nm c:=chlorophyll concentration

α:=specific absorption coefficient @λ=685 and 730 nm d:=leaf thickness

A:=constant, also containing the coefficients α,β,c,d.

The fluorescence emission and the pigment absorption bands are overlapping around 685 nm (FIG. 3), hence the emitted (fluorescence-) photons are reabsorbed selectively during their path through the leaf tissue resulting in an exponential dependence of the ratio F685/F730 from the parameter: mean free light path in the leaf, scattering coefficient and chlorophyll concentration. FIG. 3 shows a diagram of the shape of specific absorption (α) of chlorophyll a and the corresponding fluorescence emission spectrum (Ψ).

The only time dependent variation found in the ratio occurred during the transitions from fully dark adapted plants to light adaptation. This small variation was shown to occur from dark to early morning, from afternoon to evening and during Kautzky kinetic. Under day light no significant dependence or correlation respectively of the red fluorescence ratio and global irradiation could be found. Therefore it is assumed that these changes are related to variations in the optical properties of the leaf tissue. A potential mechanism could be the orientation of the plant organelles (e.g. chloroplasts) towards the arising illumination, but this is matter of further investigations.

Nevertheless, the ratio gives access to measure relative variations of the chlorophyll concentration for a plant species if one assumes a similar morphology for the individual plants. This means that the leaf internal scattering coefficient and the leaf geometry are comparable.

Mazzinghi (EP 0 434 644 B1, 1991 and P. Mazzinghi: "A laser diode fluorometer for field measurements of the F685/F730 chlorophyll fluorescence ratio" in "REVIEW OF SCIENTIFIC INSTRUMENTS", Vol.67, No. 10, October 1996, pages 3737–3744, XP000635835, New York, USA) developed an "instrument for the two-channel measurements of the fluorescence of chlorophyll". This portable and compact system is dedicated for direct contact measurements of the fluorescence ratio F690/F730 (respectively F685/F730) as well as for measurements of the $R_{FD}$-value at both wavelengths using a helium neon laser or a laser diode as continuous excitation source. When operated in full sunlight the residual background light (passive spectrum), due to the direct reflection of the leaf, must be checked after each measurement separately (and then subtracted) because this light is not completely eliminated by the filter on the probe.

The blue-green fluorescence BG will be discussed now.

The origin of the BG fluorescence is more difficult to identify and is still matter of scientific discussion. The blue-green fluorescence originates mainly from the cell walls in the upper layer of leaves and only a small fraction is emitted from deeper cell layers.

For chloroplasts no blue fluorescence is evident because the red chlorophyll fluorescence is the dominant factor. Nevertheless it is known that NADPH in the chloroplasts is emitting blue fluorescence. Also on the cell level it is shown that fluorescent co-enzymes such as NADH or NAD(P)H are very sensitive bio-indicators of metabolic functions such as the degradation of glucose or respiration. Thus the blue NADPH emission depends on the physiological state of the plant.

For leaves the emission of enzymes and co-enzymes is completely covered by emission of the cell wall where several pant constituents are embedded. As is well-known plant phenolics, ferulic-, chlorogenic- and caffeic acids, as well as coumarins are source of the blue emission and alkaloids and flavonols are source of the green fluorescence.

The detection and interpretation BG fluorescence intensity will be discussed now.

On the basis of the present knowledge about the BG fluorescence there is no commonly agreed interpretation of the overall BG fluorescence intensity. A lot of emitter are clearly identified but their contribution to the total signal is still unknown.

A link to the photosynthetic apparatus, comparable to the description in Equation (1), is only found for the NADPH fluorescence. Assuming a time invariant BG fluorescence of all other emission sources it could be capable to monitor also this transients of the BG fluorescence.

Generally the emission is originated at other plant components, e.g. the epidermal cell layer, especially the cell walls or at the vacuoles, also in the mesophyll cells. All this component do not contain chlorophyll and thus do not contribute to the photosynthesis. Nevertheless the main information, derivable from the BG fluorescence intensity is an estimation of the quantity of emitting plant (tissue) pigments in this spectral range.

Detection and interpretation of the parameter BG fluorescence ratio will be discussed now.

Evaluating the spectral characteristics of the BG fluorescence with special regard to the also monitored red fluorescence provides the possibility to normalize the fluorescence (to the chlorophyll fluorescence) and thus making this measurement resistant to calibration effects and signal fluctuations from successively recorded measurements.

As investigated there are at least four different effects, proved by comparable laboratory or field experiments, which can be differentiated due to the spectral characteristics in the blue, green and red range:

Distinction of mono- and dicotyledone plants (blue-green-red)

Synthesis of UV protection pigments (UV stress) (blue-red) Infection by mildew, rust, . . . (fungi) (blue-green-red)

Detection of leaf necrosis at pine needles (blue-green).

In the case of leaf surface coverage by other organic materials as e.g. during fungal infections the fluorescence emission spectrum of the infected leaf is affected in two different ways:

the auto-fluorescence of the fungi increases (or changes) the BG fluorescence selectively fungi at the surface lower the red fluorescence by absorbing the excitation light and therefore decreasing the penetration depth. The same effect is seen if the excitation light is diffusely reflected by an additional tissue layer at the plant surface.

The latter behaviour is also known from UV protecting pigments within the epidermal cell vacuoles which hinders the "UV" excitation to penetrate deeper cell layers and thus depresses the chlorophyll fluorescence selectively. Usually these pigments (e.g. anthocyanin) are solely absorbers and do not contribute to the total fluorescence signal.

The following preconditions are to satisfy for a successful data collection.

Actinic—non actinic measurement light conditions are to be considered.

Depending of the topic of interest it may be necessary to avoid an influence to the photosystem by the excitation source. In all cases where the fluorescence intensity is relevant for the measurement the excitation must keep the plant system condition. It should be controlled only by environmental parameters as e.g. solar irradiance, vitality or the healthy state.

An a priori excluded influence of the excitation allows a measurement of the illumination and thus an estimation of the vitality or healthy state respectively.

This is mostly irrelevant for measurement of the relative chlorophyll concentration because both emission bands are dependent in the same way, but already in the case of comparing the red fluorescence with the blue fluorescence the different origins of the emission bands indicate the necessity of controlling the emission intensity as far as possible.

On the other hand an undisturbed (by excitation light) photosystem gives the possibility to extract plant specific information by controlling the environmental parameter. The variation of e.g. the light energy supplied or the health state of a plant allows the determination of measurement rules to make an interpretation of the intensity fluctuations feasible. This technique is widely used in the already mentioned PAM fluorometry, or realized by the daily cycle measurements with the far field lidar system.

Beyond that the signal to background ratio (SBR) is to be considered.

The signal to background ratio for the active induced fluorescence is defined as the number of photons passively reflected by the leaf tissue (IR) plus sun induced fluorescence ($F_{Sun}$) plus the emitted fluorescence photons (stimulated by the excitation of the measurement light ($F_{add}$)) divided by the number of photons passively reflected by the leaf tissue (IR) plus sun induced fluorescence ($F_{Sun}$)

To distinguish each contribution one needs to determine both of them. In the far field lidar technique the excitation pulse is as intense that the passive background is negligible in comparison to the induced fluorescence light. The main disadvantages of this method are the high cost for an adequate excitation system (laser), the huge effort to operate the laser (power supply, eye safety restrictions, precision optics) and the uncertainty of the illumination state at the measurement plant position.

Moreover the signal to noise ratio (SNR) must be considered.

For single shot operation the signal to noise ratio defines whether a detection system is able to measure the fluorescence signal with each excitation pulse. The main source of noise defining the SNR are:

the sensitivity of the photon detector the power of the background signal ($S_{t1}$)

the power of the active fluorescence signal ($F_{laser}$)

the operating distance the entrance aperture of the detection system.

The first source is defined by the detector characteristics, whereas the other three components are dependent on the so called "shot-noise".

Photo multiplier tubes (PMTs), especially in continuous operation, are detectors with extremely low noise levels, clearly below the noise level of the photon (shot) noise even with a high gain level. With an optical system large enough to collect sufficient fluorescence photons to depress the signal distortion by shot noise allows single shot operation. This is mandatory in all cases where the target is rapidly changing.

If the target is located at a fixed position relative to the detection system one may use for instance lock-in technique to separate a noisy fluorescence signal from any noise source independently whether the origin of the noise is shot- or detector noise. In this cases one can reduce the requirements to the optical system (reduction of the aperture) or exchange the photo multiplier tube by a cheaper avalanche or normal photodiode.

A fast repetition rate fluorometer is proposed in U.S. Pat. No. 5,426,306 for measuring in-vivo fluorescence of phytoplankton or higher plants with series of fast repetition rate excitation flashes. The system induces the variable fluorescence in order to derive photosynthetic parameters such as variable fluorescence, effective absorption cross section, rate of electron flow and turnover times of photosynthesis. This device is used for measuring fluorescence of samples as a function of the series of excitation flashes.

A method for the automatic detection of plants by measuring chlorophyll fluorescence intensity was introduced by WO 91/10352. According to this method, fluorescence is excited by a light source at wavelength under 550 nm. The emitted fluorescence is detected with a camera supplied with a broadband edge filter (transmission over 600 nm and blocking below 600 nm). No active background suppression is applied. Therefore, a recommendation is given that the light source is strong enough for picture information and that the radiation of the light source reflected directly from the plant or the substrate does not reach the camera.

SUMMARY OF THE INVENTION

It is an object of the invention to provide a cheaper high performance fluorescence detection assembly reducing the necessary excitation power by use of a low power laser sufficiently powerful to stimulate emission of a measurable quantity, and reducing the influence of the background signal.

It is a further object of the present invention to provide a new technical approach to measure well known plant physiological parameters under certain conditions with the most accurate determination of the corresponding measurement and environment conditions.

According to the present invention a fluorescence detection assembly for determination of relevant vegetation parameters is characterized in that said low power laser device provided in the excitation source is a high repetitive pulsed laser device with several nanosecond pulse length and a preferred excitation wavelength in the red spectral region of preferable 670 nm, in that said dichroic beam splitter couples the formed excitation beam co-axially to the optical axis of a receiver optic and directing this formed beam witout optical waveguiding to a vegetation target subject to be investigated, in that said basic fluorescence detector system forms an image of the excitation spot at the sensitive detector area, in that said electronic detection device operates at the doubled pulse repetition rate of said excitation laser source and samples the active fluorescence signal synchronously with the laser emission on the one hand and the passive background signal with a fixed delay in the microsecond range before or after the active signal on the other hand, recording those signals by means of a fast sample and hold circuit coupled to an analog to digital converter which enables a digital signal processing, in that said electronic detection device further comprises means for determining the pure fluorescence signal by subtracting the background signal from the active fluorescence signal electronically or in a post processing procedure, and in that said electronic trigger and timing device synchronizes the laser pulses with the sample intervals of said electronic detection device.

Thus this assembly measures explicitly the background signal. The interesting fluorescence signal Flaser is calculated by subtracting the passive contribution to the total signal.

$$F_{laser} = S_{t2} - S_{t1}$$

"S" is the signal at time (subscript) "t1" and "t2"

$$S_{t1} = I_R + F_{\lambda Sun}$$

$$S_{t2} = I_R + F_{\lambda Sun} + F_{\lambda laser}.$$

At "t1" the active excitation is zero and at "t2" the active fluorescence emission is added to the passive signal.

To reduce the necessary excitation power the detection spot and thus also the excitation spot is reduced as far as the contribution of the background signal is reduced to the level of the active fluorescence signal.

These and other features and advantages of the present invention will become more apparent from the following detailed description of exemplary embodiments thereof, as illustrated in the accompanying drawings, in which:

BRIEF DESCRIPTION OF THE DRAWINGS

FIG. 6a is a side view and FIG. 6b a front view showing an arrangement of an optical extension of the detector module to record additional spectral fluorescence emission and elastic back scatter channels.

DETAILED DESCRIPTION OF PREFERRED EMBODIMENTS

Figure 4:
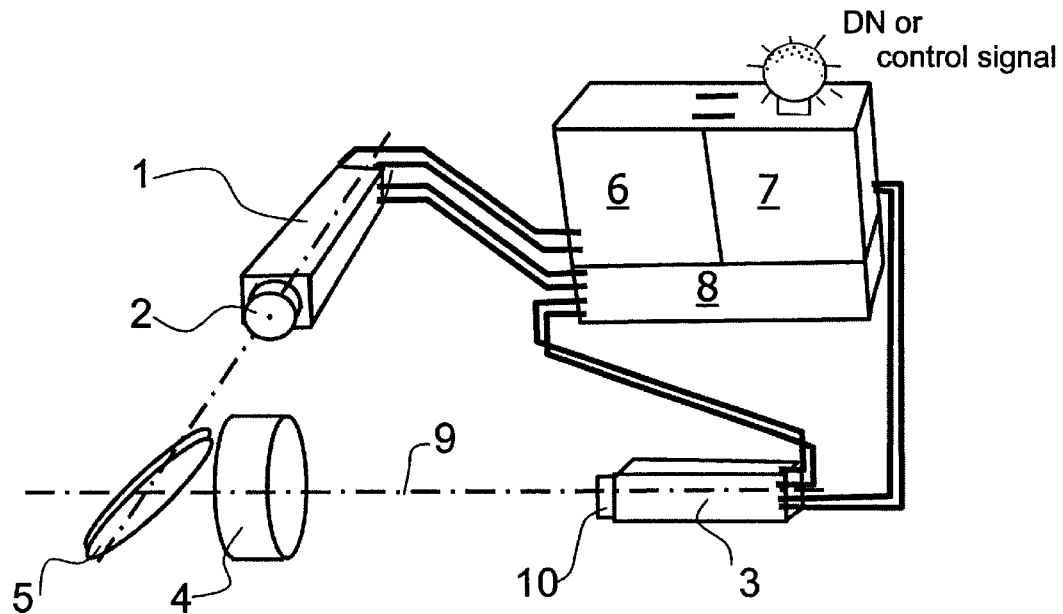
FIG. 4 is a schematic diagram showing a basic single channel assembly to detect fluorescence intensities according to the invention.

FIG. 4 shows a basic system configuration utilized for detection of chlorophyll fluorescence-intensities includes five hardware components: an excitation laser source 1 in the form of a 670 nm light emitting laser diode with beam forming optics 2, a fluorescence detector 3, including an imaging optic 4 and a channel separation optic 5, a trigger and delay electronic 6 to adjust the laser and detector timing, a detector electronic 7, consisting of a signal recording and processing module, and a power supply module 8.

The excitation source 1 is a high repetitive (1–50 kHz) low power (>0,5 W peak power) laser device, with several nanoseconds pulse length (10–50 ns). The excitation wavelength is preferable 670 nm for an efficient stimulation of chlorophyll fluorescence. With an excitation wavelength of 670 nm the strong red absorption band of chlorophyll is matched allowing highly efficient excitation. The laser beam is formed by the beam forming optics 2 containing an astigmatism correction lens (cylinder lens) and a beam expander/reducer to a point spot. Finally the beam is coupled coaxial to the optical axis 9 of the receiving detector optic 4 via a dichroic beam splitter (dichroic mirror) forming a channel separation optic 5.

The detector 3 may be a PMT (photo multiplier tube) operating in continuous mode if the system measures in single shot operation for rapidly changing targets. It may be an avalanche or photodiode if the target is fixed and the signal recording allows lock-in techniques. The entrance aperture is a spherical lens, which forms an image of the excitation spot at the masked (field-stop) sensitive area of the detector. The elastic back scatter signal is blocked out by an interference (IF) filter 10. The center wavelength of the IF filter 10 is chosen in accordance to the interesting emission wavelength anywhere in the range from 680–740 nm. The band width is not critical, a bandwidth of 10 or 15 nm is recommended. The blocking quality beside the transmission bandwidth has to be very good (>$10^3$) because the excitation wavelength is very close to the detection wavelength. The risk of signal contamination by not completely blocked excitation photons is high because the back scatter signal is some orders more intense than the interesting fluorescencte signal.

The trigger and timing electronic 6 has to drive and synchronize the laser pulse with the sample interval of the detector electronic 7. For agricultural, horticultural and greenhouse applications the pulse propagation delay can be adjusted to a fixed value, due to the stable geometry of the entire set-up. Run time variations by variable distances between the detector 3 and the target can be neglected because the expected variability of ±10 cm (and thus the variability of the beam propagation delay) is small in comparison to the length of the excitation pulse (as an example, if $\tau_{laser}$=20 ns, the variation may be extended to some meters before false triggering occurs).

Figure 1:
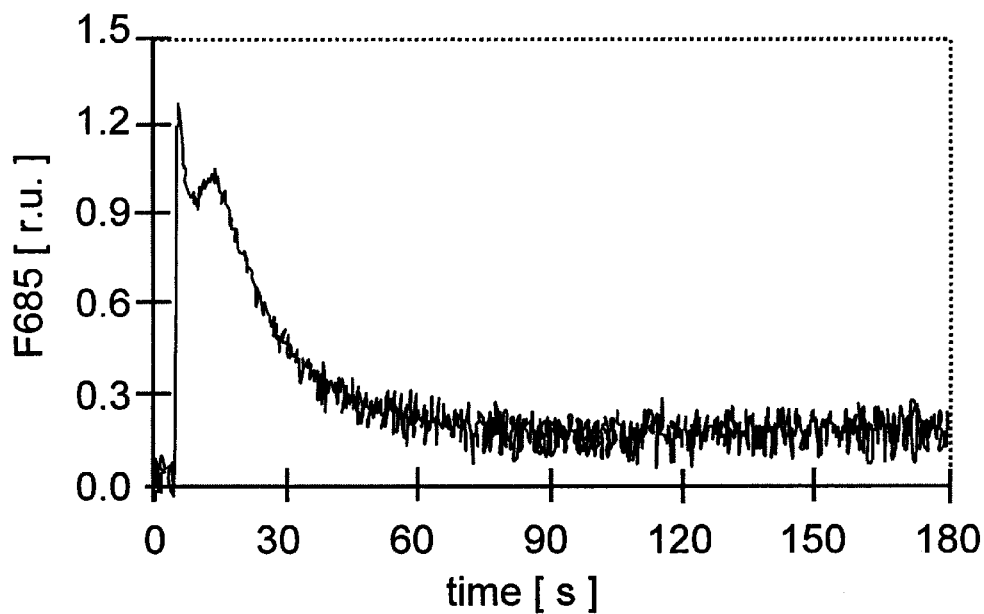
FIG. 1 is a previously discussed diagram of Kautzky kinetic.
Figure 2:
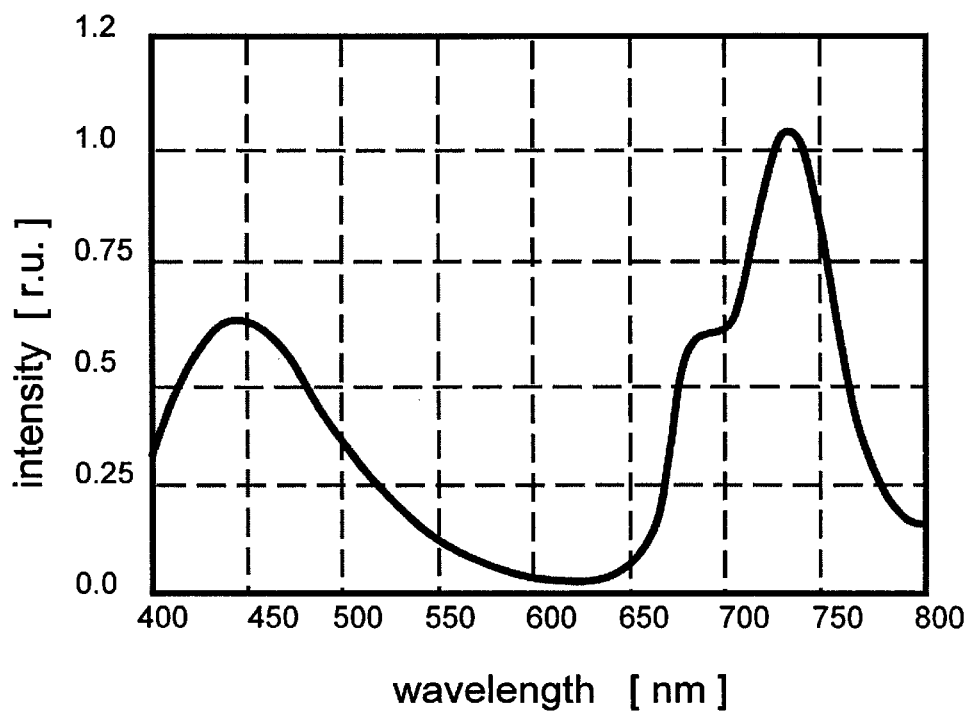
FIG. 2 is a previously discussed diagram of a special fluorescence emission spectrum.
Figure 3:
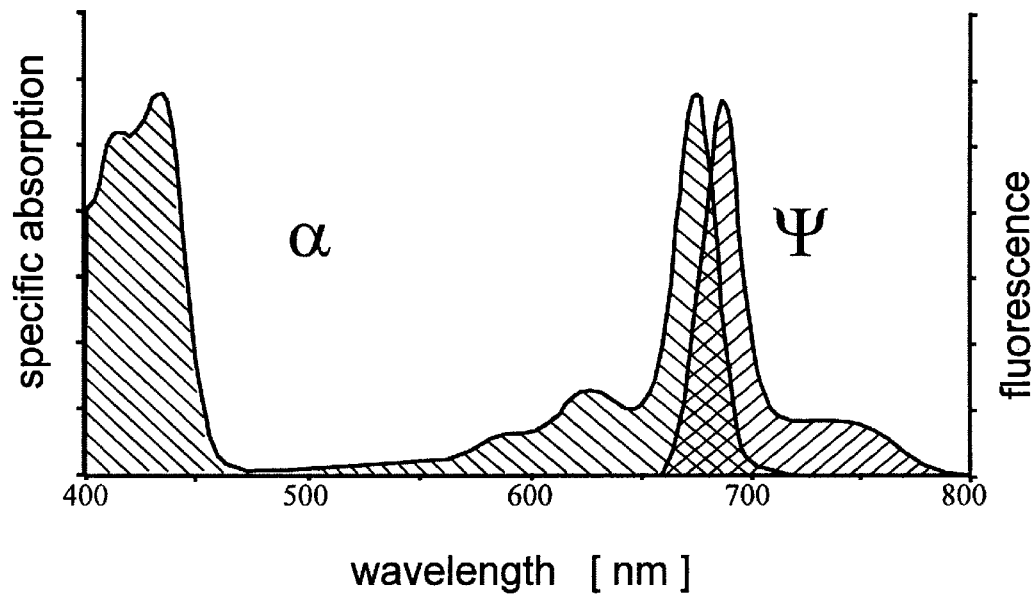
FIG. 3 is a previously discussed diagram of the shape of specific absorption ($\alpha$) of chlorophyll a and the corresponding fluorescence emission spectrum ($\Psi$)
Figure 5:
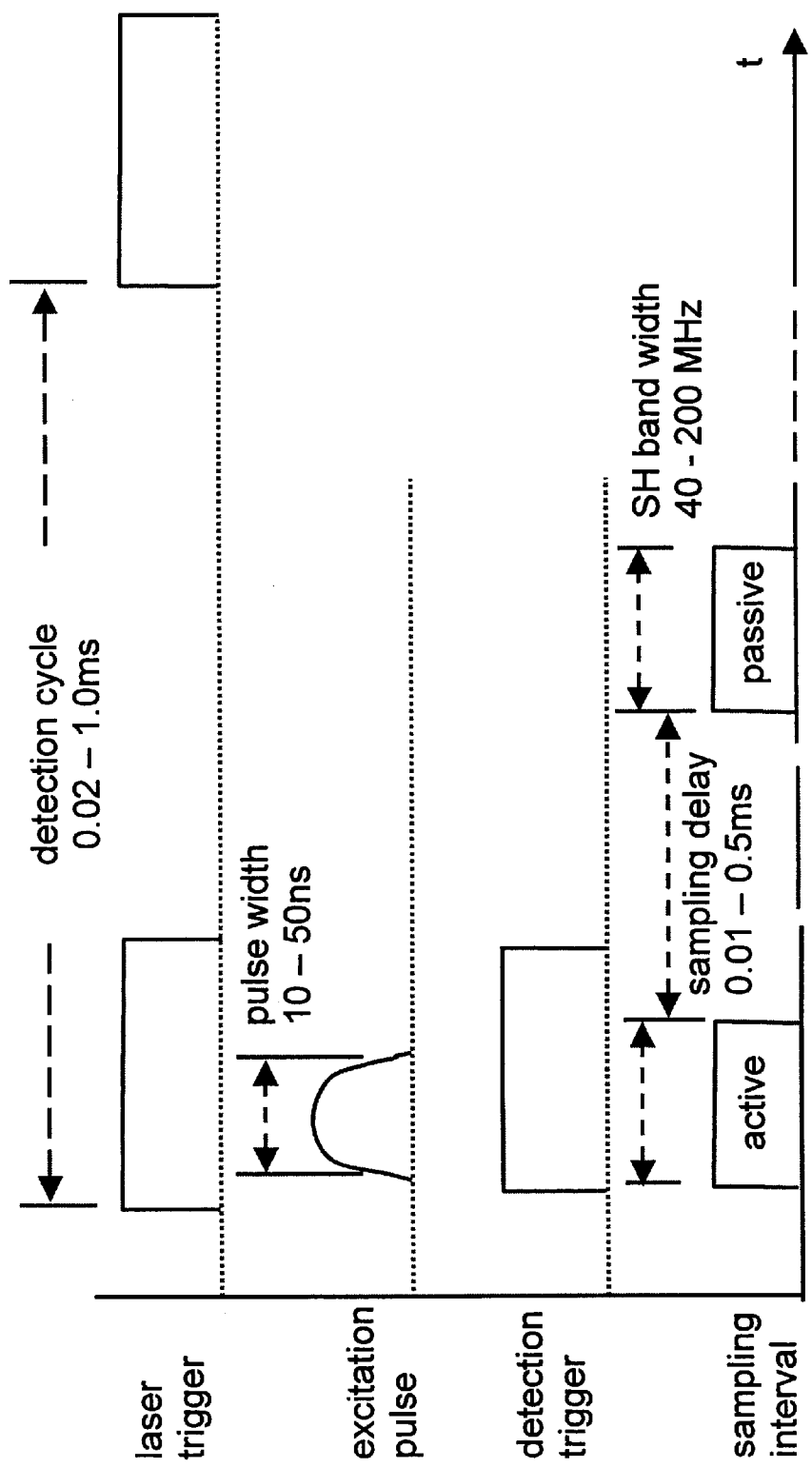
FIG. 5 is a timing diagram of the assembly according to the invention for on-line background correction (laser diode trigger and detector electronic triggering for active and passive measurements)

In order to realize a real time correction with regard to the reflected sunlight and the sun-induced fluorescence the electronic detection system operates at the doubled repetition rate of the excitation laser. FIG. 5 shows a timing diagram of the basic system illustrated in FIG. 1 for on-line background correction including laser diode trigger and detector electronic triggering for active and passive measurements. Synchronous to the laser emission the sampling interval of the active detection window (laser on: $S_{t1}$) is opened. With a fixed delay of some microseconds the passive background signal (laser off: $S_{t2}$) is recorded. In the detector electronic 7 of FIG. 4 a fast sample and hold (S&H) signal recorder with a 40–200 MHz analog bandwidth is coupled to an analog to digital converter (ADC) which enables a signal processing adapted to the special case of application. If no single shot operation is required the detector electronic 7 consists of an lock-in amplifier. Finally the power supply module 8 delivers the electrical power to the whole hardware system.

The operating distance will be more or less fixed for a specific assembly. It will range from direct contact up to 1.0 m but variable for different hardware configurations depending on the actual scope of operation. The variable operating range for an adjusted distance will be determined in the calibration procedure during the build-up process of a hardware device.

The output of the detection electronic 7 is dependent on the scope of operation. For post processing a digital number DN proportional to the recorded fluorescence signal will be delivered while an analogue signal will be given to control attached hardware components.

The determination of the chlorophyll fluorescence-ratios will be described now.

The above described "basic assembly" can be modified to monitor spectral features of the fluorescence emission. The basic assembly is supplemented by additional detector elements, including photo-detectors and sampling electronic. As FIG. 6a (side view) and 6b (front view) show the optical set-up is modified by:

Introducing dichroic mirror(s) 11 along the optical axis 12 at the detection side. The dichroic mirror(s) 11 separate the collected light in spectral fractions. In addition, this set-up guarantees the same timing characteristics for all sampling electronic(s). Also the new system can be operated on-line, just in contrast to the method and apparatus of U.S. Pat. No. 5,412,219 where a plurality of filters must be inserted sequentially in order to get the full spectral information.

The photo active areas of the additional detector(s) 13 are provided with IF filters 14 and additional blocking filters according to the required scope of operation.

The number of detection channels depends on the relevant scope of investigation. For the measurement of the chlorophyll concentration when excited with the laser diode operating at 670 nm two channels (preferable at 685 nm and 730 nm with a bandwidth of ±5 nm) are sufficient.

For monitoring blue and/or green fluorescence a second laser has to be added. The excitation wavelength can range from 355 to 400 nm with similar power and timing specifications as the red laser diode used for the chlorophyll excitation. Both excitation wavelengths have to be adjusted to hit the same area on the subject of investigation. The use of two different lasers improves the techniques used according to U.S. Pat. No. 5,412,219 and EP-0 419 425 B1.

An excitation source operating in the UV/blue (355 nm<$\lambda$<400 nm) only is not recommended. As mentioned earlier UV protecting pigments within the epidermal cell vacuoles of plants grown outdoor hinder the "UV/blue" excitation to penetrate deeper cell layers and thus depresses the chlorophyll fluorescence selectively. In most cases found under field condition, the red fluorescence signal cannot be differentiated from the long-wavelength tail of the blue/green fluorescence.

In order to detect the blue and/or green fluorescence three respectively four detectors are needed.

For plant identification an additional detector is necessary to record the elastic backscatter signal at the wavelength of the red laser diode (at 670 nm).

For recording leaf surface layers or infections (see later) another detector may be added to record the elastic backscatter signal of the UV excitation.

For measuring the leaf internal light scattering a laser diode operating in the NIR wavelength range (800 nm<$\lambda$<1000 nm) may be added and a corresponding detector will measure the elastic backscatter signal.

All signals are recorded by similar detection electronics. For scientific application they are prepared for post processing via analog to digital conversion and transfer to a computer system. If the system is used for the controlling (automatization) of any machinery an internal micro controller will evaluate and interpret the recorded data set and produce a corresponding control signal which is transmitted to the attached equipment.

The recording of ancillary parameter will be described now.

Depending on the application it is necessary to determine environmental (E), additional plant (P) and system (S) parameters e.g.:

laser diode pulse energy(ies) (S)

(solar) irradiance at the position of the sensor (E)

canopy top level (P)

canopy high (P).

The laser pulse energy has to be monitored if the pulse to pulse stability (PPS) or the long term stability of the excitation source is poor. The red laser diode used for chlorophyll fluorescence excitation has a PPS of 3%. Therefore the stability is sufficient and the installation of an energy monitor is not recommended.

In applications where the energy has to be monitored an additional photodiode is installed in the optical path at the excitation side which detects any stray light (usually sufficient to trace the energy fluctuations). The diode output signal is also fed into the electronic module, where an energy correction of the fluorescence and backscatter signals is performed.

The (solar) irradiance (PAR) at the position of the system is relevant for the interpretation of the chlorophyll fluorescence intensity. Therefore one PAR sensor, located above the canopy and not obscured should be installed. The PAR signal at the fluorescence sensor (within the canopy) will be recorded by the detection electronic (at the specified wavelength bands and without excitation, e.g. background signal) and act as additional information source in the post processing or in the micro controller algorithms.

For the correct interpretation of plant fluorescence it is often necessary to know where the measurements were taken (position of the sensor above or within the canopy). Therefore, if the fluorescence detection system is used for agricultural applications (e.g. mounted on a vehicle) the detection system must be located relative to the canopy top level. The canopy top level will be monitored continuously by a vertical movable light bar which is horizontally oriented relative to the canopy surface. The position of the light bar and thus the position of the fluorescence detector is moved vertically according to a duty cycle. The duty cycle defined as the number of dark-light transitions per time interval of the light bar signal determines if the light bar is moved down or up. For adjusting the duty cycle the speed of the vehicle must be taken into account. When the duty cycle is lower than a given number (assuming that the sensor is- above the canopy then no light-dark transition occurs), the sensor is moved down slowly until the duty cycle exceeds a maximum value. The "vertical actors" for the movement of the light bar-sensor package might be hydraulic, pneumatic or mechanical elements.

Measuring the relative canopy top level by the apparatus described above, the absolute canopy height can be determined when the distance of the sensor to the ground is known.

APPLICATIONS OF THE INVENTION

A device for the detection for chlorophyll containing plants or plant organs and robotic plant identification will be described now.

An apparatus for the detection of green vegetation (characterized by chlorophyll) can be realized by using one excitation source, preferably a laser diode operating at 670 nm and one detector (PMT or diode) with an interference filter transmitting at a wavelength in the range from 680 to 740 nm with a spectral bandwidth between 5 and 25 nm.

Using the above described electronic for on-line detection of background signals and automatic on-line correction of the background signals the sensor can be operated in full sunlight. Using a suitable threshold vegetation can be identified without any further signal processing. Chlorophyll produces nearly exclusively a fluorescence signal in this wavelength range (under natural conditions). The contrast between vegetated and non vegetated targets will be extremely high. It is not necessary to monitor the excitation energy and the illumination conditions at the plant position. The plant position is defined by the position and orientation of the detector head which are known a priori.

Possible applications of this detection assembly are:
steering systems for greenhouse or horticulture robots;
plant (weed) detection systems with subsequent plant destruction; this sensor system is interesting for fast and continuous identification of weeds growing on railways and on-line cleaning of the railways by applying specific chemicals, hot water or others.

The first application is interesting in combination with any distance sensor or three dimensional terrain monitoring systems, to identify whether a target is green vegetation (a plant) or not.

The benefit of this method of plant detection is manifested by the fact that pattern recognition or spectral analyses is not necessary.

A device for the determination of chlorophyll concentrations will be described now.

The first extension of the prior described apparatus allows the determination of relative changes (chronological or locally distribution) of the chlorophyll concentration per leaf area. To realize this a second detection channel is added to the basic assembly as described above. The spectral detection bands are 680–690±5 nm and 720–740±5 or 10 nm. The fluorescence signals are corrected on-line from the background signals (passive signal) and then the background corrected signals are divided. A multiplication with a calibration factor specific for the plants under investigation gives absolute chlorophyll values:

$$\frac{S_{\lambda 1(active)} - S_{\lambda 1(passive)}}{S_{\lambda 2(active)} - S_{\lambda 2(passive)}} * C_{calibration} = C_{Chlorophyll}.$$

It should be noted that the calibration values are depending on the light adaptation of the plants. When the environmental light level changes in a way that plants make transients from light adapted to dark adapted photosynthetic status and vice versa the calibration values might be wrong.

This set-up is useful e.g. for the greenhouse robots if the chlorophyll status will be recorded to describe the growth (development) state or long term stress conditions of plants. This technique is also applicable at any chlorophyll containing material as e.g. chlorophyll containing epidermal fruit skins during their development. Especially the state of maturity can be determined when fruits lose their typical green color (e.g. cherry, banana, apple, nuts, etc.). Also monitoring chlorophyll concentration by fluorescence allows monitoring the decay of fresh fruits (if they contain chlorophyll in their skin) and vegetation if aging (e.g. storage time) is accompanied by chlorosis (chlorophyll transformation in chemical fragments). Examples are cucumber, some apple types or salad leaves.

A device to control site specific fertilization will be described now.

It is known that the chlorophyll concentration of leaves is dependent and thus correlated on the nitrogen and sulfur concentration of the whole plant. Fertilizer deficiencies are visible by characteristic reduction of the chlorophyll concentration (except in the case of nitrogen fertilizer over saturation). In the case of wheat this fertilization effects are nutrient specific located more in the upper leaf layers (nitrogen) or lower layers (sulfur) of the canopy.

Two other effects are observable under the influence of distinct fertilization levels. The plants show a gained growth speed (plant size) and they also show characteristic changes in the production of bio mass and plant (leaf) density.

A sensor concept, feasible to monitor all these parameter is again based on the previously described dual channel diode laser fluorosensor. The detector head is mounted to a movable "robot" arm which is fixed at a moving platform (e.g. vehicle). The vertical position of the arm is regulated by the light bar mentioned above, which determines the actual "surface" of the total canopy. Thus the absolute canopy height could easily be determined by the knowledge of the initial detector height relative to the soil. The detector head will be adjusted relative to this surface level, or periodically move anywhere in the range between soil and surface level. This periodic movement could be a vertical oscillation or a rotation at a spinning wheel. Taking into account the horizontal movement of the carrier platform (tractor) a two or in the case of rotation three dimensional profile could be monitored in terms of vegetation presence (fluorescence signal recorded: YES/NO) and chlorophyll concentration (rationing the two fluorescence detection channels). Joining the a priori determined position data for each measurement, the recorded canopy height and the leaf parameters allow the calculation of all previously discussed canopy parameters: canopy height, canopy density and chlorophyll concentration, as well as their two (or three) dimensional distribution inside the vertical measurement layer (or measurement volume).

A device for differentiation between monocotyledon and dicotyledon plants for controlled weed specific herbicide treatment will be described now.

In cases where weeds are the only plants at any agricultural or horticultural site (as e.g. in the case of early appearing weed, before the culture plant is growing) it is sufficient to know the precise plant position for a suitable treatment. For this purpose it is enough to utilize the basic assembly with a scanner extension.

If both plant types are growing at the same time and site (competing) one has to distinguish weed and culture plants. In many cases these plant types are separable in monocotyledon (MC) and dicotyledon (DC) plants for which selective herbicides can be applied.

Investigating the fluorescence emission spectra from 400 to 750 nm it is shown that DC plants have generally a significant reduced blue fluorescence emission in comparison to MC plants. This feature will be used to distinguish both plant types.

To excite efficiently the blue fluorescence an additional excitation source has to be implemented to the assembly. It was found that an ideal laser source operates at about 400 nm. Shorter excitation wavelengths are mostly absorbed in the upper leaf layers and thus do not excite the photosystems (red fluorescence) very efficient. Only light sources around 400 nm excite both, red and blue fluorescence sufficiently and would be the best choice for the entire system, but they are presently not commercially available. Nevertheless this problem can be overcome by using two excitation lasers simultaneously. A compact Nd:YAG laser operating at 355 nm or any other UV emitting laser is suitable while the red laser diode is kept in the system for exciting the red fluorescence. In this case an inter-calibration has to be performed to normalize the fluorescence intensities which is mandatory for the ratio interpretation.

On the detection side it is necessary to install at least one additional detector module with a center wavelength in the range between 430 and 460 nm (bandwidth not critical 10–50 nm). A fourth detector module can monitor the fluorescence signal in the green wavelength, because an advanced plant distinction is possible due to characteristic fluorescence emissions (in this wavelength range) at several vegetation types.

The open field assembly should be a scanning system, which is again (as in the case of nutrient supply) mounted at a robot arm whose position is regulated relative to the simultaneous monitored canopy top level.

The recorded fluorescence ratios: F400+x(blue)–F680+x (red) and F500+x(green)–F680+x(red) are interpreted with regard to the environmental light conditions because the red fluorescence intensity is, in contrast to the blue/green fluorescence, dependent on the status of the reaction centers.

The comparison with predefined (calibrated) thresholds for the spectral feature will be used to determine the weed density or in the case of a scan over the entire soil surface the precise distribution of the plants (Plant type [X,Y,Z]). This position information will be fed into the regulation device of the weed disruption system.

a device for the detection of various fungal infections and controlled fungicide treatment will be described now.

The detection of fungal infection needs an assembly with two excitation sources plus the second detection band in the red fluorescence region and one detector for the elastic backscatter signal at 355 or 670 nm. The latter could already be monitored by a simple photodiode due to the expected high signal level in comparison to the fluorescence signal.

With this assembly many different plant-fungi interactions can be monitored:

Effects on the photosynthetic system will be recognized by changes in the photosynthetic activity and thus by variations in the fluorescence intensity in one of the red detection channels. A similar candidate of this infection type is already found in the case of mildew infection, where the photosynthetic system is influenced in an early phase of fungi development by a significantly reduced response time in the Kautzky kinetic.

Fungal infection can result in changes in the leaf morphological structure, total cell destruction or variations in the composition of the plant pigment constituents. Morphological variations (and thus of the leaf optical properties) or reduction in the chlorophyll content will be determined by the channel ratio of the red detection bands.

Specially in the case of inhomogeneous infections (e.g. by rust infection) the distribution over the total leaf area can be determined and provides an additional (quantitative) identification criteria.

Changes in the composition of blue and/or green fluorescence (BG) emitting pigments will be recognized by the detection channels in this range. This strategy will be as successful as in the case of weed distinction if one assumes monocultural plant canopies. Additionally some fungi are characteristic sources of BG fluorescence themselves (e.g. mildew) and can thus be discovered directly or even identified by their BG emission feature.

Mildew covers in a late development phase the leaf surface with an additional tissue layer and causes the typical whitish look. This induces a significantly increased surface reflectance and can thus be measured by the elastic back scatter signal at the red excitation wavelength as well as at the UV excitation.

Finally a fluorescence system installed at a robot arm with a vertical (perhaps three dimensional) moving capability provides the possibility to determine the vertical distribution of the fungal infection, which is also characteristic of several fungi types.

It is not expected to identify all different types of fungal infection, but under certain conditions the number of candidates is limited and thus this technique will be adequate as early warning system or steering device for plant protection system.

Finally a device to monitor the photosynthetic activity of vegetation by time series will be described.

This developmental step introduces the interpretation of the chlorophyll fluorescence intensity into the whole detection assembly. The technical realization is dependent on the measurement requirements. This could be the simple comparison of relative variations of fluorescence intensities, normalized to the relative chlorophyll content, or the more advanced but complex determination of photosynthetic ability as performed e.g. in the Kautzky kinetic or in the PAM fluorometry.

The measurement of relative variations can be performed in the spatial as well as in the time domain. The hardware assembly is in both cases identical to the basic assembly, but the interpretation algorithm has changed to:

$$\left(1 \Big/ \frac{S_{\lambda 1(active)} - S_{\lambda 1(passive)}}{S_{\lambda 2(active)} - S_{\lambda 2(passive)}}\right) * (S_{\lambda 2(active)} - S_{\lambda 2(passive)}) = RPA.$$

RPA is the relative photosynthetic activity. The target material is assumed to be homogeneous distributed. A priori RPA is dependent on the time and the geometric location RPA(t;x,y,z). Thus the related experiment has to be performed under controlled environmental conditions. The installation of the PAR sensor will give information about the environmental light condition close to the detector head but not interfered by the target material (shadowed or indirectly illuminated).

This device is useful for application where the status of plants should be monitored, in terms of vitality or healthy state etc. One application is the investigation of long term processes, where the interaction of a well defined sample plant (or sample set) with variable environmental conditions will be observed. Another application is the investigation of a large number of targets under controlled light conditions in e.g. a greenhouse or laboratory.

To determine the more complex photosynthesis kinetic parameter the requirement to the light conditions are more restricted. The Kautzky kinetic and thus all related parameter can only be measured with dark adapted plant, this means during night time or in the laboratory. To perform this measurements it is necessary to keep the excitation spot fixed to see the response to actinic light in the time domain. The source of actinic light can be the excitation source itself if the repetition rate is increased as far as the average illumination induces an actinic reaction. The actinic effect could also be triggered by an extra white light source which illuminates the plant with a continuous photon flux, starting at a precise determined time mark. With the first technique ($S_{\lambda(passive)}=0$) the evaluation is reduced to an arithmetic of pure fluorescence signals. The second one is also possible without any technical changes because the passive signal ($S_{\lambda(passive)}>0$) is fully under control by the system.

From the PAM fluorometry it is known, that the so called "Genty-Parameter" (GP) is a good measure of the quantum yield of $CO_2$ assimilation. The Genty-Parameter can be obtained by measuring the steady state fluorescence (called: Fs) as well as the steady state fluorescence superimposed by a saturating light pulse (called: Fm'):

$$\frac{(Fm' - Fs)}{Fm'} = GP.$$

A high value of the GP indicates a high electron flux in the electron transfer chain while low values may reflect disturbances in the photosynthetic system when the fluorescence is measured under the same environmental conditions (especially under the same light intensities).

The steady state fluorescence Fs will be excited remotely by the laser diode while an additional white lamp or the sun act as actinic light. Fm' will be generated by an additional strong light source (flash lamp).

Due to the PAR sensor and the detection of the passive background signal this fluorescence system will be able to monitor Fs and Fm'. Thus the GP as a function of irradiance can be monitored reflecting the $CO_2$ assimilation without applying any equipment for gas analysis. The switching between actinic and saturating light quantities will be performed preferably by modulating the same source from continuous background light to high illumination pulses of several milliseconds.

The assembly according the present invention provides a new technical approach to measure well known plant physiological parameters under certain conditions with the most accurate determination of the corresponding measurement and environment conditions.

What is claimed is:

1. Fluorescence detection assembly for determination of relevant vegetation parameters comprising an excitation source (1) consisting in a low power laser device with an excitation wavelength in the red spectral region, a beam forming optical device (2), a dichroic beam splitter (5), a basic fluorescence detector system (3) including an entrance optical device (4) receiving fluorescence emission via said dichroic beam splitter (5) and an interference filter (10) blocking out the elastic back scatter signal, an electronic detection device (7) for detecting a fluorescence signal, andy an electronic trigger and timing device (6), characterized in that said low power laser device provided in the excitation source (1) is a high repetitive pulsed laser device with several nanosecond pulse length and a preferred excitation wavelength in the red spectral region of preferable 670 nm, in that said dichroic beam splitter (5) couples the formed excitation beam co-axially to the optical axis (9) of a receiver optic and directing this formed beam without optical waveguiding to a vegetation target subject to be investigated, in that said basic fluorescence detector system (3) forms an image of the excitation spot at the sensitive detector area, in that said electronic detection device operates at the doubled pulse repetition rate of said excitation laser source (1) and samples the active fluorescence signal synchronously with the laser emission on the one hand and the passive background signal with a fixed delay in the microsecond range before or after the active signal on the other hand, recording those signals by means of a fast sample and hold circuit coupled to an analog to digital converter which enables a digital signal processing, in that said electronic detection device (7) further comprises means for determining the pure fluorescence signal by subtracting the background signal from the active fluorescence signal electronically or in a post processing procedure, and in that said electronic trigger and timing device (6) synchronizes the laser pulses with the sample intervals of said electronic detection device (7).

2. Fluorescence detection assembly according to claim 1 wherein said laser device (1) is a laser diode operating in the red spectral region.

3. Fluorescence detection assembly according to claim 1 or claim 2 wherein the power of said laser device (1) is chosen >0.5 W peak power.

4. Fluorescence detection assembly according to claims 1 or 2 wherein a second laser is added for monitoring blue and/or green fluorescence, the excitation wavelength of said second laser being fixed in the range from 350 to 400 nm, with similar power and timing specifications as the red laser excitation source.

5. Flourescene detection assembly according to claim 3 wherein a second laser is added for monitoring blue and/or green flourescene, the excitation wavelength of said second laser being fixed in the range from 350 to 400 nm, with similar power and timing specifications as the red laser excitation source.

6. Fluorescence detection assembly according to claim 1 wherein said beam forming device (2) comprises an astigmatism correction lens and a beam expander/reducer to a point spot.

7. Fluorescence detection assembly according to claim 1 wherein said fluorescence detector (3) is a photo multiplier tube operating in continuous mode.

8. Fluorescence detection assembly according to claim 1 wherein said fluorescence detector (3) is an avalanche diode.

9. Fluorescence detection assembly according to claim 1 wherein said fluorescence detector (3) is a standard photo diode.

10. Fluorescence detection assembly according to claim 1 wherein said entrance optical device (4) comprises in its aperture a spheric lens, which forms an image of the excitation spot at the masked sensitive area of said fluorescence detector (3).

11. Fluorescence detection assembly according to claim 1 wherein the center wavelength and bandwidth of said interference filter (10) is chosen appropriately in the range from 680–740 nm, the blocking quality beside the transmission being more than $10^{-3}$.

12. Fluorescence detection assembly according to claim 1 wherein said sample and hold circuit has an analog bandwidth chosen appropriately between 40 and 200 MHz.

13. Fluorescence detection assembly according to claim 1 wherein said basic fluorescence detector system (3) is supplemented by additional detector elements (13), and additional dichroic beam splitters (11) are provided to the optical axis (12) at the detection side to form specific fluorescence detection bands, the number, center wavelength and bandwidth thereof depending on the scope of investigation.

14. Fluorescence detection assembly according to claim 13 wherein said basic fluorescence detector system comprises two detection devices having first and second detection channels located at 680–690±5 nm and 720–740±5 or 10 nm, respectively.

15. A method for determination of chlorophyll concentrations with the fluorescence detection assembly according to claim 14, comprising dividing background corrected signals, determining changes of the relative chlorophyll content per leaf area, and determining the absolute chlorophyll concentrations by multiplying the ratio of fluorescence emission in the first channel to fluorescence emission in the second channel with a predetermined calibration factor.

16. A method comprising determining the chlorophyll status of plants and thus describing the growth state or long term stress conditions of plants, with the fluorescence detection assembly according to claim 14 together with greenhouse robots.

17. A method comprising determining the state of maturity of any chlorophyll containing material when specific fruits lose their typical green color, with the fluorescence detection assembly according to claim 14.

18. A method comprising observing changes in the chlorophyll concentration any chlorophyll containing material whereby decay monitoring of fresh fruits, if they contain chlorophyll in their skin, and vegetation is practicable, with the fluorescence detection assembly according to claim 14.

19. Fluorescence detection assembly according to claim 14 wherein said basic fluorescence detector system comprises a detector head located at a movable "robot" arm (X-Y components) which is mounted at a moving platform which provides a third movement component (Z-component).

20. A method comprising controlling site specific fertilization with the fluorescence detection assembly according to claim 19, said step of controlling being based on the fact that chlorophyll concentration of leaves is dependent and thus correlated on the nitrogen and sulfur supply of the whole plant so that fertilizer deficiencies are visible by characteristic reduction and distributions of the chlorophyll concentration which effect is accompanied by reduced growth speed and characteristic changes in the plant density.

21. A method carried out with the fluorescence detection assembly according to claim 19, comprising regulating the vertical position of the "robot" arm by a light bar which determines an actual upper canopy level and wherein the detector head is adjusted relative to the upper canopy level, or moves between soil and the upper canopy level.

22. A method comprising monitoring the three dimensional profile of the relevant vegetation parameters with the fluorescence detection assembly according to claim 19, wherein said monitoring step is carried out to take into account the horizontal movement of said moving platform.

23. Fluorescence detection assembly according to claim 19, further comprising an additional excitation source exciting efficiently the blue fluorescence and performing an inter-calibration of the two excitation sources to normalize the fluorescence intensities to the excitation pulse power, said assembly further comprising a detector module with a center wavelength in the range between 430 and 460 nm ($\Delta\lambda$=10–50 nm).

24. Fluorescence detection assembly according to claim 23 wherein said additional excitation source is a triplet Nd:YAG laser 355 nm.

25. Fluorescence detection assembly according to claim 23 comprising additional detector modules monitoring the green fluorescence (500–550 nm; $\Delta\lambda$=10–50 nm) to improve the knowledge about the spectral emission feature of the occurring plant types.

26. Fluorescence detection assembly according to claim 23, further comprising a PAR sensor to monitor the illumination environment and thus to interpret band ratios with regard to environmental light conditions.

27. A method for differentiation between monocotyledon and dicotyledon plants with the fluorescence detection assembly according to claim 23, comprising distinguishing the monocotyledon (MC) and dicotyledon (DC) plant types by their characteristic feature of the fluorescence emission spectra from 400 to 750 nm, said step distinguishing comprising measuring the blue fluorescence relative to the red chlorophyll emission.

28. The method of claim 27, further comprising providing a predetermined ratio threshold defining whether a signal belongs to a MC or DC plant.

29. The method of claim 27 comprising providing a classification algorithm, in the case of programmable post processing, defining whether a signal belongs to a MC or DC plant.

30. A method for performing site specific herbicide treatment in terms of weed position and type, comprising detecting relevant vegetation parameters with the fluorescence detection assembly according to claim 23.

31. A method for detection of various fungal infections, comprising: detecting relevant vegetation parameters with the fluorescence detection assembly according to claim 23 extended by the second detection band in the red fluorescence region; and using one detector package to monitor the elastic back scatter signal.

32. Method according to claim 31, further comprising recognizing effects on the photosynthetic system by changes in the fluorescence intensity.

33. Method according to claim 31, further comprising further comprising determining changes in leaf morphological structure, total cell destruction or variations in the composition of plant pigment constituents by determining the channel ratio of the red detection bands, and provides an additional quantitative identification criterion based on inhomogeneous infections and their characteristic distribution over total leaf area or canopy.

34. Method according to claim 31 further comprising recognizing changes in the composition of blue and/or green fluorescence emitting pigments as a result of infection by the detection channels in this range, for discovering some fungi that are characteristic sources of blue and/or green fluorescence.

35. Method according to claim 31, further comprising recognizing leaf surfaces that are covered with an additional tissue layer causing a significantly increased surface reflectance, by observing the elastic back scatter signal at the red as well as at the UV excitation wavelengths.

36. Method according to claim 31 applied to site specific fungicide treatment based on fungi position and type.

37. A method comprising monitoring the photosynthetic activity of vegetation by time series with the fluorescence detection assembly according to claim 14, wherein the investigated target is variable.

38. Fluorescence detection assembly according to claim 1 further comprising two additional detectors recording the elastic back scatter signal at the emission wavelengths of the laser sources.

39. Fluorescence detection assembly according to claim 1 comprising an additional photodiode, installed in the optical path at the excitation system monitoring the laser pulse energy.

40. Fluorescence detection assembly according to claim 1 comprising a PAR(photosynthetic active radiation)-sensor located above the measurement position monitoring the environmental light conditions.

41. Fluorescence detection assembly according to claim 1 comprising a vertically movable, horizontally oriented light bar determining the canopy top level and thus plant height, the vertical position of the basic fluorescence detector system being coupled with said light bar and being fixed or moving relative to it.

42. Fluorescence detection assembly according to claim 41 comprising hydraulic, pneumatic or mechanical elements realizing the movement of said light bar as well as said basic fluorescence detector system.

43. Flourescene detection assembly according to claim 1 wherein said beam forming device (2) comprises a cylinder lens and a beam expander/reducer to a point spot.

44. Fluorescence detection assembly according to claim 1, further comprising a detector head mounted to a movable robot arm, and a moving carrier platform to which said robot arm is fixed, and wherein said laser device is an excitation laser diode operating at 670 nm, said basic fluorescence detector system comprises a detector module, and said interference filter transmits at a wavelength in the range from 680 to 740 nm with a spectral bandwidth between 5 and 25 nm.

45. A method for detection of chlorophyll containing plants or plant organs (plant recognition), i.e. green vegetation, with the fluorescence detection assembly according to claim 44, comprising using a suitable threshold to recognize vegetation, such that the contrast between vegetated and non vegetated targets is sufficiently high that a recognition is done without any further signal processing.

46. A method for determination of relevant vegetation parameters with the fluorescence detection assembly according to claim 44, comprising defining a plant position relative to the position of the detector head and determining the distribution of plant material by assuming a controlled two or three dimensional movement of the carrier platform.

47. A steering system for greenhouse or horticulture robots comprising the fluorescence detection assembly according to claim 44.

48. A method for detecting and destroying plants comprising: detecting plants with the fluorescence detection assembly according to claim 44, and destroying plants that are detected.

49. A method comprising monitoring the photosynthetic activity of vegetation by time series with the fluorescence detection assembly according to claim 44, wherein the investigated target is fixed and thus the variation is only time dependent.

50. Method according to claim 49 or claim 37, further comprising determining the environmental light condition utilizing a PAR sensor.

51. Method according to claim 49 or claim 37 wherein digitized fluorescence values are interpreted with respect to the existing illumination situation and history while post processing.

52. Method according to claim 49 for scientific investigation of long term processes, comprising investigating the interaction of plants and variable environmental conditions.

53. Method according to claim 49 for scientific investigation of the Kautzky kinetic and all related parameters which can only be measured at a dark adapted plant, at a fixed position.

54. Method according to claim 53, comprising utilizing the excitation source as a source of actinic light and increasing repetition rate of pulses from the excitaiton source to induce an actinic reaction.

55. Method according to claim 53, comprising utilizing a triggering extra white light source, which illuminates the vegetation at a determined time, as a source of actinic light.

56. Method according to claim 49 for scientific investigation of the Genty-Parameter, comprising measuring steady state fluorescence as well as steady state fluorescence superimposed on a saturating light pulse.

57. Method according to claim 56, comprising exciting the steady state fluorescence (Fs) remotely by a laser diode while using an additional white lamp or the sun to act as actinic light, and generating the saturating light pulse (Fm') by an additional light source such for monitoring Fs and Fm' and the intensity of the saturating light based on detection of a passive background signal.

* * * * *